United States Patent [19]

Kataoka et al.

[11] Patent Number: 5,041,989

[45] Date of Patent: Aug. 20, 1991

[54] METHOD AND APPARATUS FOR OBSERVING OPERATING STATE OF MECHANICAL SEAL

[75] Inventors: Tadashi Kataoka, Yokohama; Yashuhide Hisada, Chiba; Masahiro Komatu, Ichihara, all of Japan

[73] Assignees: Ebara Corporation; Cosmo Oil Company, both of Tokyo, Japan

[21] Appl. No.: 184,883

[22] Filed: Apr. 22, 1988

[30] Foreign Application Priority Data

Apr. 28, 1987 [JP] Japan .................. 62-103372

[51] Int. Cl.[5] .................. G06F 15/20; G01N 29/00
[52] U.S. Cl. .................. 364/507; 73/587; 73/593; 73/600; 73/660; 340/679
[58] Field of Search .......... 73/600, 588, 660, 579, 73/587, 593; 364/508, 507; 340/683, 679

[56] References Cited

U.S. PATENT DOCUMENTS

| | | |
|---|---|---|
| 3,034,043 | 5/1962 | Dega . |
| 4,337,660 | 7/1982 | Weiss ........................ 73/600 |
| 4,493,042 | 1/1985 | Shima et al. ................ 364/507 |
| 4,584,879 | 4/1986 | Webster et al. ............. 73/588 |
| 4,615,216 | 10/1986 | Wykoupil . |
| 4,696,191 | 9/1987 | Claytor et al. ............. 73/600 |
| 4,748,850 | 6/1988 | Kataoka ..................... 73/660 |

FOREIGN PATENT DOCUMENTS

| | | |
|---|---|---|
| 98353 | 7/1980 | Japan . |
| 837527 | 6/1960 | United Kingdom . |
| 2035560 | 6/1980 | United Kingdom . |
| 2064771 | 6/1981 | United Kingdom . |
| 2082324 | 3/1982 | United Kingdom . |
| 2104658 | 3/1983 | United Kingdom . |
| 2188422 | 9/1987 | United Kingdom . |

OTHER PUBLICATIONS

"Development and Experience with Computerized Acoustic Incipient Failure Detection (IFD) Systems", H. P. Bloch, ASME pp. 77-Pet-2.
Patent Abstracts of Japan, vol. 4, No. 149 (P-32) (631), Oct. 21, 1980; & JP-A-55098 353 (Hitachi Seisakusho K.K.) 26-07-1980.
IEEE Transactions on Industry Applications vol. IA-20, No. 3, Part 1, May/Jun. 1984, pp. 519-527, New York, USA; J. T. Renwick: "Condition Monitoring of Machinery Using Computerized Vibration Signature Analysis" FIG. 7, Table III.

Primary Examiner—Parshotam S. Lall
Assistant Examiner—V. Trans
Attorney, Agent, or Firm—Oblon, Spivak, McClelland, Maier & Neustadt

[57] ABSTRACT

A method and an apparatus for observing operating state of a mechanical seal are disclosed. The apparatus comprises a sensor 1, amplifier 2,4, a root mean square value voltmeter 5 and a computer 7. Root mean square values of outputs of high frequency acoustic emission generated by a mechanical seal provided on a rotary machine are inputted in the computer 7 which performs operations to obtain a maximum value, a minimum value, a mean value and deviation of the continously measured root mean square values. The computer also computes the magnitude of each of the values, any tendency for variation thereof and their mutual relationships, whereby the operating state of the mechanical seal is judged in terms of damage of and the possibility of leakage of sealed fluid from the sliding surfaces of the mechanical seal.

3 Claims, 6 Drawing Sheets

METHOD AND APPARATUS FOR OBSERVING OPERATING STATE OF MECHANICAL SEAL

BACKGROUND OF THE INVENTION

The present invention relates to a method and an apparatus for observing with the passage of time the state of a mechanical seal provided on a rotary machine while the rotary machine is being operated.

With a rotary machine in which a mechanical seal is used as a shaft seal, any excessive leakage of sealed fluid due to mechanical seal failure would possibly lead to disasterous results such as fire, environmental pollution or the like, or to halting of plant operations.

Despite this, no effective method has yet materialized for observing readily and with certainty the state of a mechanical seal during operations. Due to this, a troublesome daily tour of inspection has had to be performed in order to spot any mechanical seal trouble at an early stage, or mechanical seals have been changed well before any trouble is likely to occur in order to obviate any mechanical seal trouble. Thus, inspection and maintenance of mechanical seals has required much effort and much expense.

As previously stated, performing a regular inspection as mentioned above involves a high labour cost, and every time inspection of a mechanical seal is performed, the rotary machine has to be halted. In addition, there has been a tendency for mechanical seals to be changed well before their life is over because of the risk of trouble occurring even when it is regarded as being serviceable for a further period, which is of course wasteful.

SUMMARY OF THE INVENTION

An object of the present invention is to provide a method and an apparatus for observing a mechanical seal during operations in order to spot any abnormal state such as damage thereof or the possibility of leakage of sealed fluid therefrom and thereby to predict impending failure of the mechanical seal in advance or at an early stage.

To solve the problems encountered in the prior art, the present invention provides a method for observing the operating state of a mechanical seal which comprises the steps of measuring with the passage of time root mean square (RMS) values of high frequency acoustic emission (AE) generated by a mechanical seal provided on a rotary machine while the mechanical seal is in operation, performing operations to obtain a maximum value, a minimum value, a mean value and deviation of root mean square values within a specific duration of time, predicting, on the basis of either the magnitude of the values obtained through the operation, any tendency toward variation thereof, or integrated values calculated from those values, damage of or the possibility of leakage of sealed fluid from the sliding surfaces of the mechanical seal, and performing observation by judging from the predicted state whether or not the mechanical seal is in a normal state.

The present invention also provides an apparatus for observing the operating state of a mechanical seal, which comprises:

an acoustic emission sensor for measuring high frequency acoustic emission generated by a mechanical seal provided on a rotary machine while said mechanical seal is in operation;

amplifier means for amplifying outputs from the acoustic emission sensor;

a root mean square value voltmeter for converting amplified outputs from the amplifier means into root mean square values;

a computer means performing operations to obtain a maximum value, a minimum value, a mean value and deviation of said root mean square values within a specific duration of time, and predicting, on the basis of either the magnitude of the values obtained through the operation, any tendency toward variation thereof, or integrated values calculated from those values, damage of or the possibility of leakage of sealed fluid from the sliding surfaces of said mechanical seal; and display means for representing the values obtained and the results of predicting by the computer.

The present invention constructed as described above operates as follows.

The operation of the present invention was checked and confirmed by the inventors by performing extended research and a series of experiments to solve the above-mentioned problems encountered by the prior art.

The inventors' research and experiments disclosed that the amplitude and fluctuating period of high frequency acoustic emission generated by a mechanical seal in operation varies widely depending on the condition in which the machine is operated or the sliding state of the mechanical seal. Moreover, in order to grasp the characteristics of widely varying high frequency acoustic emission in relation to the state of a mechanical seal, it was confirmed to be effective to measure the root mean square values of high frequency acoustic emission with the passage of time, to perform operations in order to obtain a maximum value, a minimum value, a mean value and any deviation in the series of measured values, and to evaluate these computed values by synthesis.

For example, when a mechanical seal is in a stable and good operating state, a mean value, a value representing deviation and the difference between a maximum value and a minimum value are small, and it is seen that each value stays at a certain level for a long time. In contrast to this, when a mechanical seal is in an unstable state, the value representing deviation becomes larger and each value fluctuates. When high frequency acoustic emission with a large amplitude are intermittently generated by intermittent development of wear caused by extraneous substances biting into the mechanical seal, the maximum value becomes extremely large as compared with the mean value, whereas when remarkable wear develops continuously due to dry friction, the mean value becomes larger. When leakage occurs from the mechanical seal, the minimum value only or the minimum, mean and maximum values become extremely low. This is because the amplitude of high frequency acoustic emission becomes lower due to a reduction in the amount of contact force acting on the sliding surfaces due to an excessive liquid film intermittently or continuously formed thereon.

The inventors' research and experiments revealed that the mean value of the computed values and the amount of wear of a mechanical seal bear a proportional relationship. Wear rate is able to be estimated from the mean value on the basis of this relationship, and the amount of wear may also be estimated by adding up the mean values.

As described above, observation of a mechanical seal is performed by evaluating the magnitude of each computed value, any tendency toward variation thereof, the mutual relationship therebetween, and the sum thereof by way of synthesis, predicting on the basis of the evaluation damage of or the possibility of leakage of sealed fluid from the sliding surfaces of the mechanical seal, and eventually judging whether the mechanical seal is operating under normal or abnormal state.

DESCRIPTION OF THE PREFERRED EMBODIMENTS

Referring to the accompanying drawings, one embodiment of the present invention will be described below.

Figure 1:
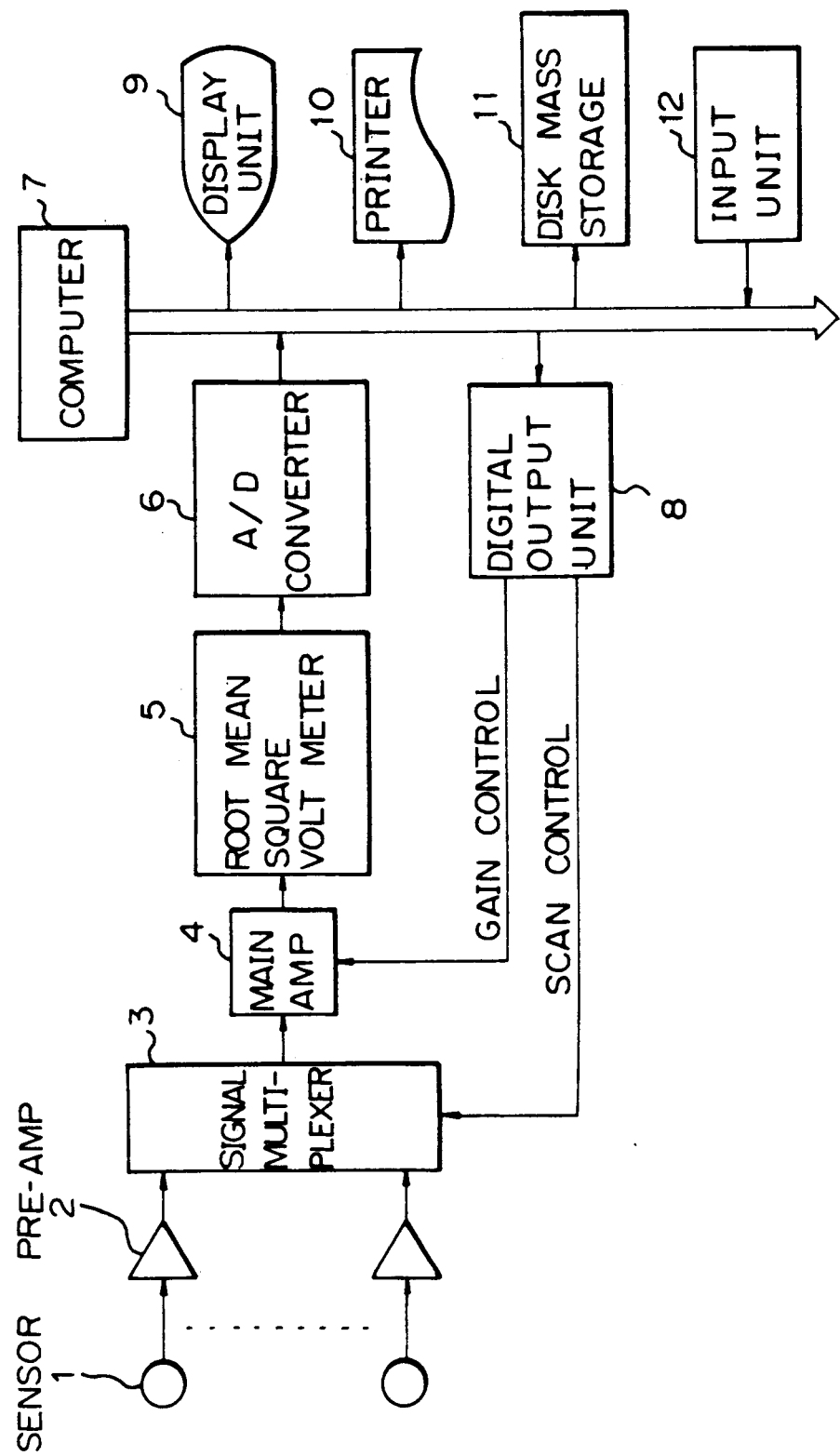
FIG. 1 shows a block diagram of an embodiment in accordance with the present invention.

FIG. 1 is a block diagram of a device in accordance with the present invention for observing the operating state of a mechanical seal. A high frequency acoustic emission sensor (AE sensor) 1 is mounted at a suitable position on a rotary machine having mechanical seals, such as a pump. An output from the high frequency acoustic emission sensor 1 is amplified by a preamplifier 2, and then reaches a main amplifier 4 via a signal multiplexer 3 to be amplified. The amplified output is converted into a root mean square value by a root mean square value voltmeter 5, and then reaches to be input into a computer 7 via an analog to digital converter 6. In synchronism with this, the signal multiplexer 3 and the main amplifier 4 are controlled by the computer 7 via a digital output unit 8 to thereby select a sensor to be used for measurement and the most suitable amplifying ratio. The computer 7 performs operations to obtain a maximum value, a minimum value, a mean value and deviation of the continuously measured root mean square values within a predetermined period of time, and computes and evaluates on the basis of an algorithm and a reference value the magnitude of each computed value, any tendency for variation thereof and their mutual relationship, whereby the operating state of a mechanical seal is judged in terms of damage of and the possibility of leakage of sealed fluid from the sliding surfaces thereof, the results of the judgement such as "halt", "normal", "caution" and "abnormal" and the resulting data not only being displayed on a display unit 9 such as a CRT and printed out by a printer 10 but also being stored in a memory device 11 such as a disk mass storage. In addition, the data with respect to maintenance and inspection of a mechanical seal is input from an input device 12 such as a key board for comparison with the measured data and the results of judgement, whereby the accuracy of the judgement of state is improved.

Referring to the examples of integrated measured data, operation of the device constructed as described above for observing the operating state of a mechanical seal constructed will be now described.

Figure 2:
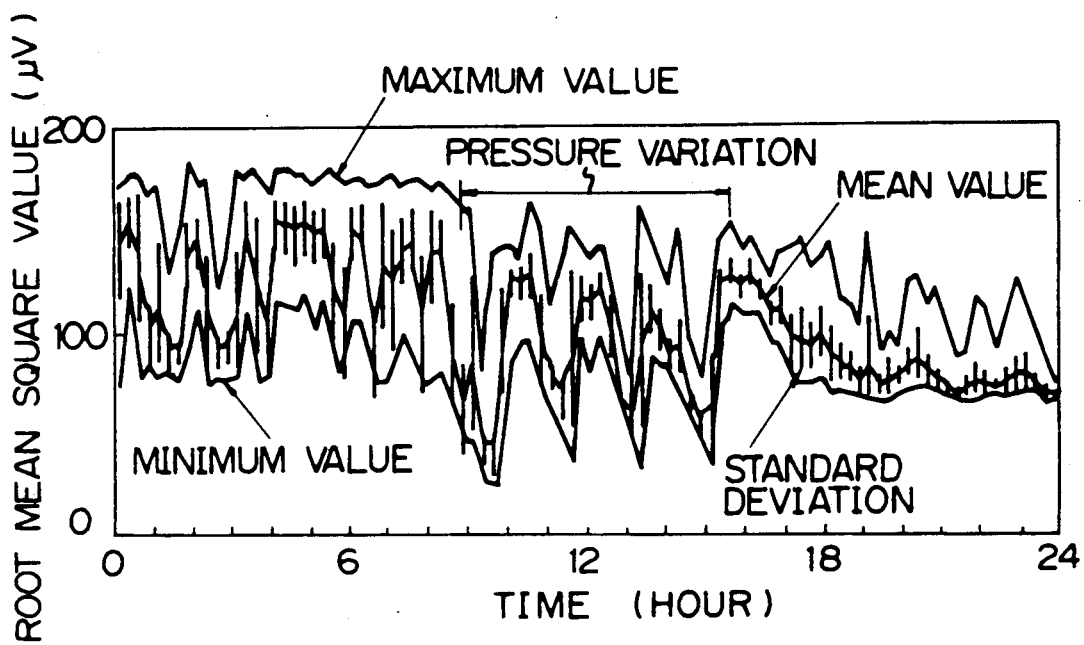
FIGS. 2 to 6 are diagrammatic views showing examples of data displays.

FIG. 2 shows an example of data display in a display unit, wherein the root mean square value level has been plotted against the time. As shown in the figure, the maximum value, the minimum value and the mean value are represented by respective continuous lines, and the deviation value by vertical lines extending by 1 $\sigma$ (standard deviation value) on either side of the mean value which acts as a reference point.

This figure shows the data taken when four great changes in pressure took place between 9 a.m. (0900) and 3 p.m. (1500). From this data it can be seen how each value varied according to the rises and falls in pressure. Generally, when the pressure is high, the contact pressure on the sliding surfaces, i.e. the load, becomes large, and the level of the mean value and the like becomes high.

In addition, as seen from the figure, although the pressure remained in a uniform condition, individual values were not necessarily uniform, and the magnitude of each value, as well as the changing condition thereof, was different. This is because, as stated previously, these values are closely related to the operating state of a mechanical seal, namely, the friction/lubrication state thereof, and this involves the fact that the state of the mechanical seal was changing in spite of the uniform operating conditions of the machine such as a pump. As described above, with the present invention, accurate observation of the operating state of a mechanical seal can be performed, this having been impossible with the prior arts.

The following are methods of judging the operating state of a mechanical seal on the basis of these data.

Figure 3:
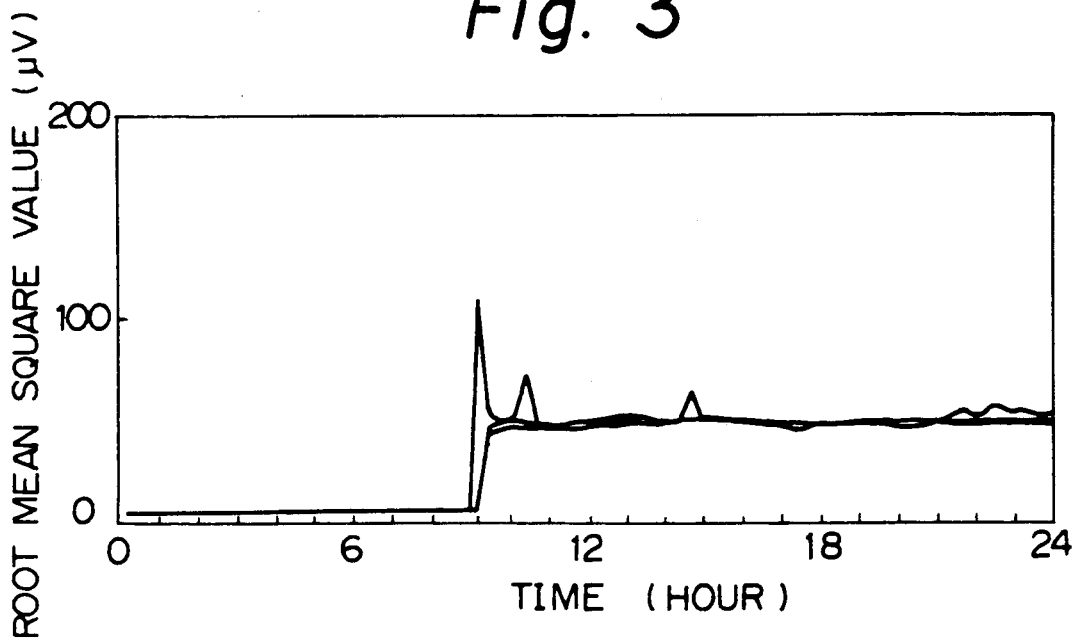

Illustrated in FIG. 3 is data showing the start-up state of a certain mechanical seal. Operation of the seal was started at 9 a.m. (0900) and proceeded thereafter. While the mechanical seal remained in a halted state, only an extremely low value determined by the noise level of the measuring instrument system was indicated, with almost no fluctuation. In a halted state, individual values remained substantially at a certain level. Thus, if set in a computer in advance, the halted and operating state can be distinguished. This judgement is useful in accurately integrating the actual operating time of the mechanical seal.

This data on the start-up point shows that the maximum value hit its peak immediately after the mechanical seal started to operate. Although this involves the fact that initial wear occurred at the start-up point, individual values remained at a relatively low level and in a stable and extremely good condition thereafter, so the computer judged that the mechanical seal was operating under a "normal" state.

Figure 4:
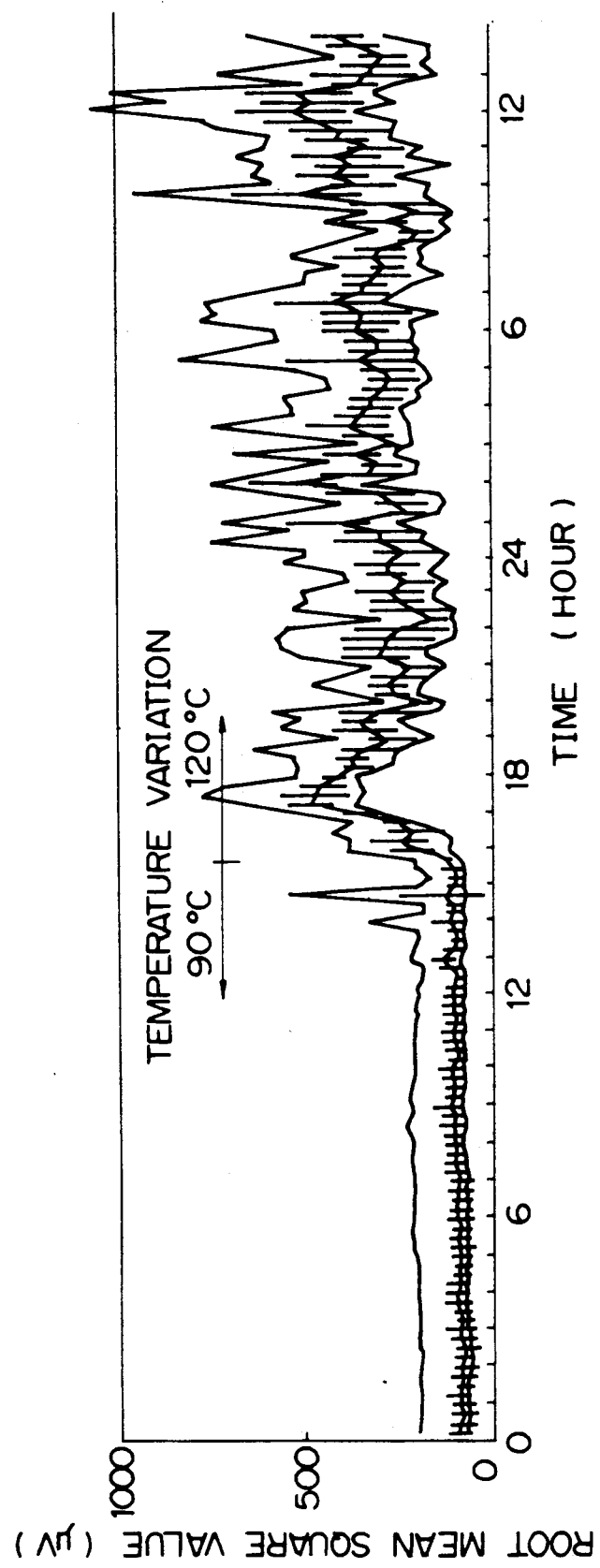

FIG. 4 shows data taken for two days with respect to a mechanical seal which experienced changes in temperatures condition. This data indicates that the temperature started to increase at about 2 p.m. (1400) on the first day, when the mechanical seal appeared to be in a state wherein flushing was at a halt, and that it reached a level ranging from 90° C. to substantially 120° C. at 5 p.m. (1700). Although they changed at certain levels before the increase in temperature started, as the temperature gradually increased, a change occurred in the maximum and deviation values first, and then the mean value and the other values also started to change. The higher level of the values and the larger degree of fluctuation thereof indicates that the mechanical seal is in an abnormal state. Under this condition, the computer judged the state as being a state of "caution" at 2:45 p.m. (1445), when a change occurred in the maximum and deviation values, and judged all states as being "abnormal" at and after 5 p.m. (1700), when the mean value reached a certain level.

Figure 5:
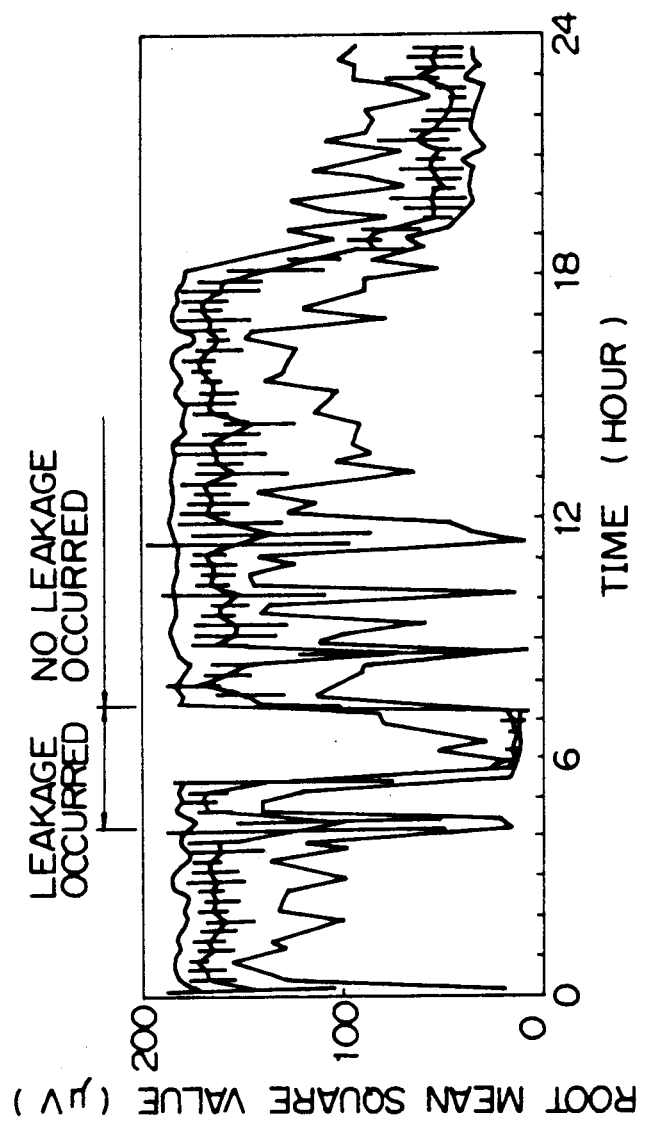

FIG. 5 illustrates data showing a state wherein a temporary leakage occurred. The leakage occurred only between 4 a.m. (0400) and 7 a.m. (0700), and at 12:00 midnight (0000) and 4 a.m. (0400), the minimum value was extremely low and close to the noise level, while the deviation value became high at 12:00 midnight (0000) and 4 a.m. (0400). At this stage, the computer judged the state as being a state of "caution", and judged the state as being a state of "abnormal" at 5:30 a.m. (0530), when the deviation and the maximum values both became extremely low. However, when the mean value increased, the computer judged that the state had been restored to "caution", and after that the state was judged as being "normal" except when the minimum value decreased to an extremely low level. Although the mean value decreased after 6 p.m. (1800), the computer judged the state as being "normal", since it was maintained at a certain level.

Figure 6:
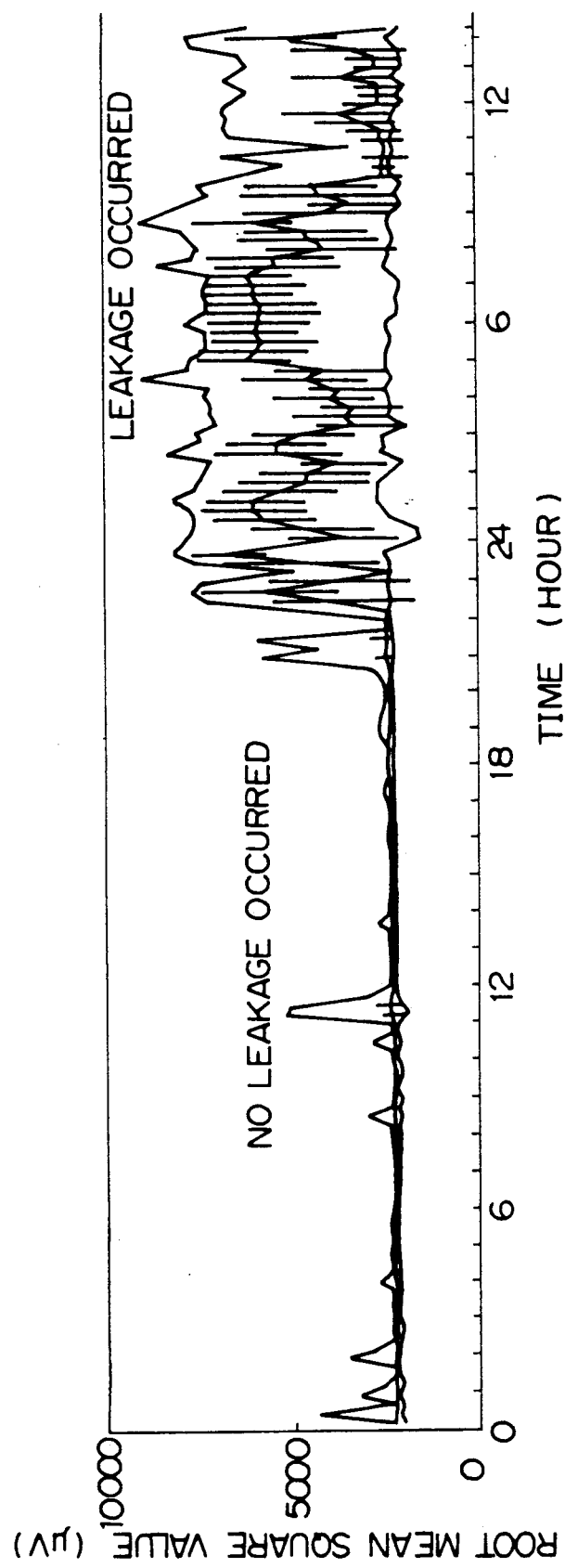

FIG. 6 illustrates data showing a state wherein intermittent leakage occurred. Although a stable state had been maintained until a clearly abnormal state was indicated, the "caution" judgement had been continuously made due to the high level of the mean value. The "abnormal" judgement was made at about 11 a.m. (1100) on the first day when the maximum value increased and the same judgement was made for all conditions after 9 p.m. (2100) on the same day. The leakage was confirmed after 8 a.m. (0800) on the second day. In this case, the leakage took place when the wear and roughness on the sliding surfaces developed to such an extent as to exceed a certain limit. As previously described, this example shows a case where an abnormal state can be detected in advance by evaluating the data indicating a drastic change in the frictional state.

Figure 7:
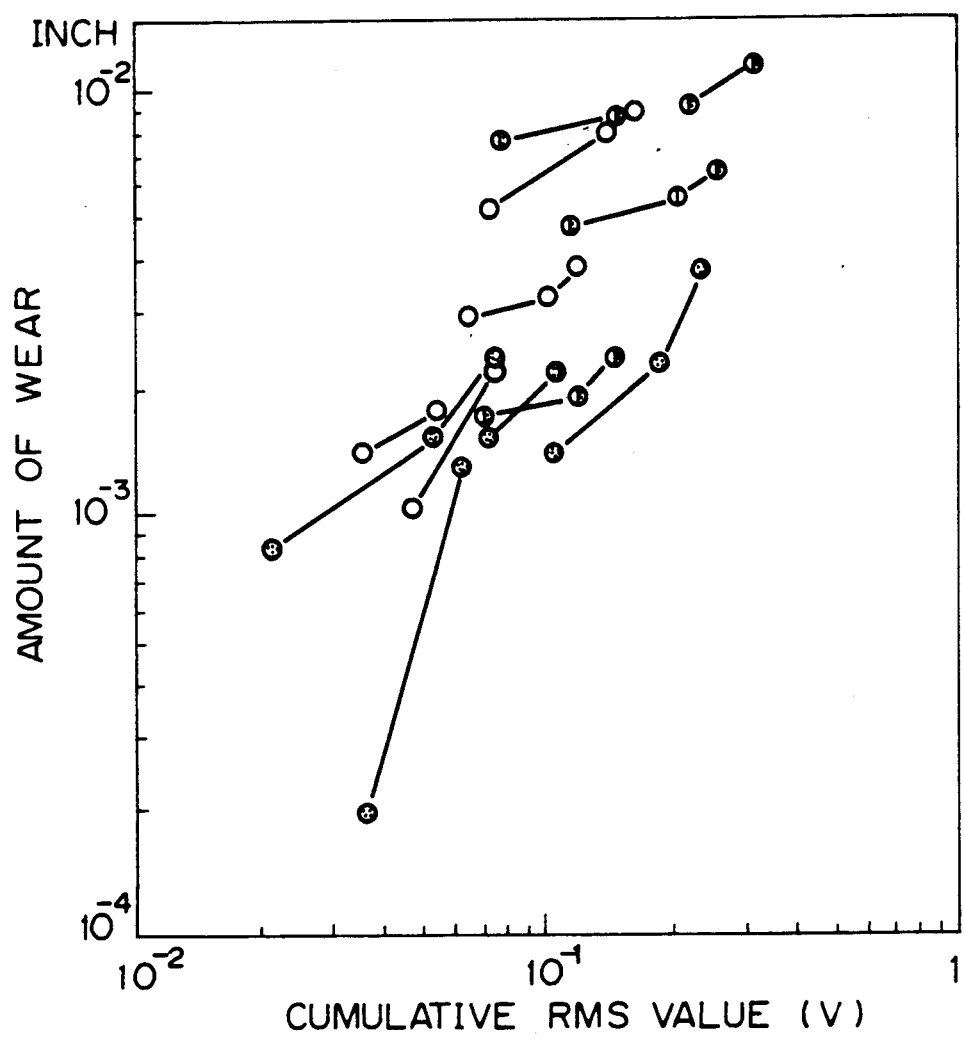
FIG. 7 is a diagrammatic view showing the relationship between the integrated value resulting from the mean values of the root mean square values of acoustic emission (AE) within a specific period of time and the amount of wear of a mechanical seal.

FIG. 7 shows one example of the experimental data. In the figure, the amount of wear of a mechanical seal is plotted against the integrated value for mean values. As seen from the figure, the amount of wear of a mechanical seal and the integrated value for mean values bear a substantially proportional relationship. On the basis of this relationship, the wear rate and the amount of wear of a mechanical seal can respectively be estimated from the data with respect to the mean values and the integrated value. The computer is designed to obtain an integrated value for the mean values of a mechanical seal from the start-up point thereof and to display an estimated amount of wear.

This invention enables observation of the operating state of a mechanical seal for damage of or the possibility of leakage of sealed fluid from the sliding surfaces thereof to thereby allow detecting of any failure in advance or at an early stage. In addition, this invention makes it possible to store data on high frequency acoustic emission generated by a mechanical seal and data on maintenance and inspection of a mechanical seal as data for use in operations, as reference data in making comparisons, and so forth. Thus, the maintenance and inspection of a mechanical seal, which has previously been dependent on an expert's experience and has involved a great deal of labour and expense, can be performed accurately and efficiently.

What is claimed is:

1. A method for observing operation of a mechanical seal on a rotary machine comprising the steps of:
    measuring, with the passage of time, root means square values of high frequency acoustic emissions generated by said mechanical seal provided on the rotary machine while said mechanical seal is in operation;
    obtaining a maximum value, a minimum value, a mean value and deviation of said measured root mean square values within a specific duration of time;
    predicting, on the basis of the magnitude of the maximum value, the minimum value, the mean value and the deviation of said measured root means square values obtained, any tendency toward variation of the maximum value, the minimum value, the mean value and the deviation of said measured root mean square values obtained, and integrated values calculated from the maximum value, the minimum value, the mean value or the deviation of said measured root means square values obtained, a possibility of damage or leakage of sealed fluid from sliding surfaces of said mechanical seal; and
    performing an observation of said mechanical seal when judging from predicted possibility that the mechanical seal is not operating under a normal state, the observation including at least one of checking for leakage of sealed fluid and checking for physical damage of said mechanical seal.

2. An apparatus for observing the operation of a mechanical seal provided on a rotary machine, which comprises:
    an acoustic emission sensor for measuring high frequency acoustic emission sensor for measuring high frequency acoustic emissions generated by said mechanical seal provided on said rotary machine while said mechanical seal is in operation;
    amplifier means for amplifying outputs from the acoustic emission sensor;
    a root mean square value voltmeter for converting amplified outputs from the amplifier means into root mean square values;
    computer means for performing operations to obtain a maximum value, a minimum value, a mean value and deviation of said root means square values within a specific duration of time, and for predicting, on the basis of the magnitude of the maximum value, the minimum value, the means value and the deviation of said root means square values obtained, any tendency toward variation of the maximum value, the minimum value, the mean value or the deviation of the said root mean square values, and integrated values calculated from the maximum value, minimum value, the mean value and the deviation of said root mean square values, a possibility of damage or leakage of sealed fluid from sliding surfaces of said mechanical seal; and
    display means for representing at least one of the root means square values obtained, the maximum value, the minimum value, and the mean value thereof, and the deviation of the results predicting by the computer means.

3. An apparatus according to claim 2, wherein outputs of the acoustic emission sensor reach the amplifier means via a signal multiplexer, and the signal multiplexer and the amplifier means are controlled by the computer to thereby select a sensor to be used for measurement and the most suitable amplifying ratio.

* * * * *